US011795470B2

(12) United States Patent
Arendze-Bailey et al.

(10) Patent No.: US 11,795,470 B2
(45) Date of Patent: Oct. 24, 2023

(54) DROUGHT RESISTANCE MULTIGENE CONSTRUCT

(71) Applicant: UNIVERSITY OF CAPE TOWN, Cape Town (ZA)

(72) Inventors: Bronwyn Lynn Arendze-Bailey, Diep River (ZA); Jennifer Ann Thomson, Constantia (ZA); Kershini Iyer, Sunningdale (ZA); Mohamed Suhail Rafudeen, Rylands (ZA); Revel Iyer, Sunningdale (ZA); Tamaryn Lorean Ellick, Zurich (CH)

(73) Assignee: UNIVERSITY OF CAPE TOWN, Cape Town (ZA)

( * ) Notice: Subject to any disclaimer, the term of this patent is extended or adjusted under 35 U.S.C. 154(b) by 0 days.

(21) Appl. No.: 17/697,927

(22) Filed: Mar. 18, 2022

(65) Prior Publication Data

US 2022/0204987 A1 Jun. 30, 2022

Related U.S. Application Data

(63) Continuation of application No. 16/305,793, filed as application No. PCT/IB2017/053309 on Jun. 5, 2017, now abandoned.

(30) Foreign Application Priority Data

Jun. 7, 2016 (GB) ..................................... 1609969

(51) Int. Cl.
*C12N 15/82* (2006.01)

(52) U.S. Cl.
CPC ................................ *C12N 15/8273* (2013.01)

(58) Field of Classification Search
None
See application file for complete search history.

(56) References Cited

U.S. PATENT DOCUMENTS

| | | | |
|---|---|---|---|
| 2010/0093017 | A1 | 4/2010 | Wolf et al. |
| 2012/0276527 | A1 | 11/2012 | Cohen |

FOREIGN PATENT DOCUMENTS

| | | | | |
|---|---|---|---|---|
| WO | 99/46370 A2 | 9/1999 | |
| WO | 00/11175 A1 | 3/2000 | |
| WO | 2009/060402 A2 | 5/2009 | |
| WO | 2014/037919 A1 | 3/2014 | |
| WO | WO-2014037919 A1 * | 3/2014 | .......... C07K 14/415 |
| WO | 2016/066711 A1 | 5/2016 | |

OTHER PUBLICATIONS

Thomson et al. (The development of genetically modified maize for abiotic stress tolerance, South African Journal of Botany-Suid-Afrikaans Tydskrift Virplantkunde, Foundation for Education, Science and Technology, Pretoria, SA, vol. 73, No. 3, Jul. 1, 2007, pp. 494-495).*

Kwon et al. (Korean J Genetics 26: 199-206, Jun. 2004).*

Arendze-Bailey et al. (WO 2014/037919 A1; Published Mar. 13, 2014).*

Garwe et al. (NCBI, GenBank Sequence Accession No. AY100455.1, Published Jun. 12, 2002).*

Govender et al. (NCBI, GenBank Sequence Accession No. EU333003.1, Published Jul. 2, 2008).*

Bork et al., Go hunting in sequence databases but watch out for the traps, Trends in Genetics, 12(10): 425-427 (1996).

Chen, Heterotrimeric G-proteins in plant development, Front. Biosci., 13:3321-3333 (2008).

Cheng et al., Overexpression of soybean (*Glycine max* (L.) Meer.) L34 gene leads to reduced survival to cold stress in transgenic *Arabidopsis*, Plant Mol. Biol. Rep., 28:41-48 (2010).

Dietz et al., The function of peroxiredoxins in plant organelle redox metabolism, J. Exp. Botany, 57:1697-1709 (2006).

Doerks et al., Protein annotation: detective work for function prediction, Trends in Genetics, 14(6):248-250 (1998).

Garwe et al., XVSAP1 fom Xerophyta viscosa improves osmotic-, salinity- and high-temperature-stress tolerence in *Arabidopsis*, Biotechnol. J., 1:1137-1146 (2006).

Hur et al., Overexpression of GmAKR1, a stress-induced aldo/keto reductase from soybean, retards nodule development, Mol. Cells, 27:217-233 (2009).

International Search Report and Written Opinion issued in PCT/IB2017/053309 dated Aug. 9, 2017.

Kwon et al., Genetic engineering of drought resistant potato plants by Co-intoduction of genes encoding trehalose-6-phosphate synthase and trehalose-6-phosphate phosphatase of zygosaccharomyces rouxii, Korean J. Genetics, 26:199-206 (2004).

Mundree et al., An aldose reductase homolog from the resurrection plant Xerophyta viscosa Baker, Planta., 211:693-700 (2000).

Nishimura et al., Over-expression of tobacco knotted1-type class1 homeobox genes alters various leaf morphology, Plant Cell Physiol., 41(5):583-590 (2000).

Shen et al., Identification of different temporal classes of gene expression during a cycle of desiccation in the resurrection plant, Xerophyta humilis, Department of Mol. Cell Biol., University if Cape Town, Rondebosch 7700, South Africa (Abstract Only).

Smith et al., The challenges of genome sequence annotation or "The devil is in the details", Nat. Biotech., 15:1222-1223 (1997).

Sun et al., Acquiring transgenic tobacco plants with insect resistance and glyphosate tolerance by fusion gene transformation, Plant Cell Rep., 31:1877-1887 (2012).

(Continued)

*Primary Examiner* — Vinod Kumar
(74) *Attorney, Agent, or Firm* — MARSHALL, GERSTEIN & BORUN LLP

(57) ABSTRACT

The present invention relates to a polygenic DNA construct consisting of three abiotic stress tolerance genes, separated by nucleic acids encoding FMDV 2A peptides under the control of a stress inducible promoter. The stable insertion of the construct into plants confers drought tolerance to the plants. The invention also provides for vectors, host cells, transgenic plants and transgenic seeds containing the construct.

13 Claims, 2 Drawing Sheets

Specification includes a Sequence Listing.

(56) References Cited

OTHER PUBLICATIONS

Thomson et al., The development of genetically modified maize for abiotic stress tolerance, South African Journal Botany—Suid-Afrikaans TydskriftVirplantkunde, Foundation for Education, Science and Technology, Pretoria, SA, 73(3):494-495 (2007).
Yang et al., Expression of the REB transcriptional activator in rice grains improves the yield of recombinant proteins whose genes are controlled by a Reb-responsive promoter, PNAS, 98:11438-11443 (2001).
Luke et al., Growing uses of 2A in Plant Biotechnology, Chaper 8, Intech, 165-193 (2015).
Yer Revel, Rule 1.132 Declaration filed in connection with U.S. Appl. No. 16/305,793, dated Mar. 1, 2021.
Garwe et al., "Molecular characterization of XVSAP1, a stress-responsive gene from the resurrection plant Xerophyta viscosa Baker," Journal of Experimental Botany, 54(381):191-201 (2003).
Govender et al., "Molecular and biochemical characterisation of a novel type II peroxiredoxin (XvPrx2) from the resurrection plant Xerophyta viscosa," Functional Plant Biology, 15 pages (2016).
Mundree et al., "Physiological and molecular insights into drought tolerance," African Journal of Biotechnology 1(2):28-38 (2002).
Seth, "Genetic Transformatin of Farmer Preferred Tropical Maize Varieties and Inbred Lines Using Drought Tolerance Conferring Genes Isolated from Xerophyta Viscosa," Thesis, 226 pages (2014).
Thomson et al., "The Use of African Indigenous Genes in the Development of Transgenic Maize Tolerant to Drought and Resistant to Maize Streak Virus," Biotechnology in Africa. Science Policy Reports, 7:135-155 (2014).

* cited by examiner

SEQUENCE LISTING

```
<160> NUMBER OF SEQ ID NOS: 21

<210> SEQ ID NO 1
<211> LENGTH: 3792
<212> TYPE: DNA
<213> ORGANISM: Artificial Sequence
<220> FEATURE:
<223> OTHER INFORMATION: Multigene Construct

<400> SEQUENCE: 1

actgtctggg tagctggcaa tatagagacg taaataattg tctgtaaata gggagaaatt     60

catggatcat caccctaatt cggtctttca ctcattttat catagacctg actaaagaac    120

ttggtcagag tttttactta tttaaaataa agaggacttc atggcatcca tgtgcaggta    180

cagctcccag aaaaaaaagc atgaaacacg agaggatcaa tagcattcga tctgaaacaa    240

aaggttgcag ctcaagactt tctccaaaat attaagatga tccaaagaat taccccaaga    300

tatccaacgt ataccaatgt gtataccgaa agtaagaaag ttcacgtgca ttctttgatt    360

tttctcccga gtgttctttt ctgaaatgag taaataagac tagaataaga gctaatgtat    420

tttttttcta aaaaaagttg aatgtggata caatatgatt atacattcat tagctatttt    480

aagtatattc tatttttttt ccccccaaaa gaacacaaat gtgttccgtc actttccatg    540

gagatcagat ctatcttaga attggacagg gtgcttatga tacaacttgt tcctatcaac    600

aactgcatgt tagacagcgc cgaatttaca gtcctactgg gcgccacttt tcaacccaca    660

tcatcaagat gaacaccacg ttatcttcat ccgctccaac cacatggtcc agcgccactg    720

gccaagaccg ccagccagcc aggccatcca acgtggtgca ttttctaaca ctccacgttc    780

gctgtacggc attatttctc cagccagaaa gaccgagaca gcgacgctgt tgggcgggcc    840

cgcggcctgc tctctctgct tccccatgag attcacgggc atcgctcctc gctcgtgcct    900

acgcgaccgc gccgatccac gtgacgtggc gcagcaatcg ttcttactag gcgcttgcac    960

gtgtcgttcg catgcgaagc gtccacactg ccaacgacct ccttaaatat ccttgtgata   1020

ttcgccttac gatctcacac ttcgcacgca aaggccagtc gcagatttgg gttgaatttg   1080

ctgcgttttg gcagattttg agcgagagat attagggaag ggatcaatga ggaacgaggg   1140

ttttctgaaa atgaagaccg acgttggagt cgccgacgag gtgatctccg gagatctcaa   1200

gcagcttggt gacgctgcaa agcggctagc taaacatgcg atcaagctcg gcgccagctt   1260

cggggttggc tctaccatag tccaggctat tgcttcgatc gctgctatct atttgttgat   1320

attggaccgg acaaactggc gtacaaatat cttgacatca cttctaattc catatgttta   1380

cttgagtctt ccttcagtga tattcaacct attcaggggc gacctgggca gatggctttc   1440

attcattggc gtagtaatga agctcttctt ccaccgacac ttcccagtta ccttggaact   1500

gcttgtgtct ctcattctcc tgattgtggt ttcccccact ttcattgccc acacaatcag   1560

aggcagtctc attggagtct tcatcttcct tgtcatcgcc tgctacctcc tccaagagca   1620

cattagatca gctggtggct tcaaaaacgc gttcacaaag agcaatggga tttcaaacag   1680
```

```
cgtcgggatc atcattctac tgatccaccc gatctggagc ttggtggtgt atttcctcta   1740
cacgtctttg ctgcaacttc ttgcatactc tccttcccct tgttgttgca tattatacaa   1800
taagtggttt aatttcatgc atgtttgtaa atgtgtaagc cttcatatgt attctcagtc   1860
aattgggtca tgcgtgtcca tatttttcgt gcagtttgta ttcatctatg aagctgaatt   1920
tatcgatggc agtggacagc tgttgaattt tgaccttctt aaacttgcgg gagacgtcga   1980
gtccaaccct gggcccgtcg agatggcacc gatcgcagtc ggtgaaacga tcccagacgg   2040
aacgctcgga tggttcgacg agaaggacga gttgaagcag atctcgatcc actcgctcgc   2100
cgccggaaag aagatcgtgc tcatcggtgt ccccggcgca ttcactccta cttgcagtat   2160
gcaacacgtt ccaagtttca ttgagaaagc agaggagctg aaagctaagg gcgttgatga   2220
gttccttgtt attagtgtta atgatccctt cgtgatgaag gcttggtcga aaacatatcc   2280
tgagaacaag catgtgaagt tcctagccga tggatcgggg aagtacaccc aagctcttgg   2340
cgtggaactc gatctgtccg agaaggggct cgggctccgt tcacggaggt ttgctatcct   2400
tgtagacgac ttgaaggtta aggttgcaaa tgtcgaggag ggcggagcat ttaccatttc   2460
aggtgccgat gagatcttga aggcagtcat cgatggcagt ggacagctgt tgaattttga   2520
ccttcttaaa cttgcgggag acgtcgagtc caaccctggg cccgtcgaga tggcgcatgc   2580
accgtgtttt gctgatgcga agacacagag cttcaagctc ctcagcgggc actcaatccc   2640
cgcagttggg ctcggcacgt ggaagtctgg tgacaaggcc ggcaacgccg tatacactgc   2700
catcactgag ggaggataca ggcacattga taccgcagca caatatggag tccatgaaga   2760
ggtaggcaat gctcttcaat ctgctttgaa agcagggatc aataggaagg ctttgttcgt   2820
cacatcgaaa gtatggtgcg aagatttatc acctgaaaga gttcgacctg cattgaaaaa   2880
tacacttgag gagctacaac tggattacct tgatctctac ctgattcact ggcctatcca   2940
ccttaaaaag ggcgcacaca tgcctcctga ggctggtgag gtgctagagt tcgacatagg   3000
aggagtgtgg agggaaatgg agaagctcgt caaagtaggg cttgttagag atattggtat   3060
ctctaacttc actgtgaaga aactcgaaaa acttctaaat tttgctgaaa taaagccctc   3120
ggtgtgccag atggagatgc acccgggttg gagaaacgac aagatgtttg agatttgcag   3180
gaaatatggt attcatacaa ctgcttattc acctctcgga tcttccgagc gtgatctcct   3240
cagtgatcca actgttttga agatagcaaa caagctcaac aagagcccag gtaaacttct   3300
ggtgagatgg gctgttcaaa gaggaactag tgtcatccca aaatcgacca acccggagag   3360
gataaaggag aacatccagg tcttcgggtg ggagattcct gcagaggatt tccagatttt   3420
gagcagcctt agtgaacaga agagagtctt ggatggtgaa gatctcttcg tcaacaaaac   3480
ccatggcccg ttcaggagcg ctgctgaact ctgggacggt gaagtctaag tcgacacccg   3540
atcgttcaaa catttggcaa taaagtttct taagattgaa tcctgttgcc ggtcttgcga   3600
tgattatcat ataatttctg ttgaattacg ttaagcatgt aataattaac atgtaatgca   3660
tgacgttatt tatgagatgg gtttttatga ttagagtccc gcaattatac atttaatacg   3720
cgatagaaaa caaaatatag cgcgcaaact aggataaatt atcgcgcgcg gtgtcatcta   3780
tgttactaga tc                                                       3792
```

<210> SEQ ID NO 2
<211> LENGTH: 1120
<212> TYPE: DNA
<213> ORGANISM: Artificial Sequence
<220> FEATURE:

-continued

<223> OTHER INFORMATION: Truncated pSap1D Promoter

<400> SEQUENCE: 2

```
actgtctggg tagctggcaa tatagagacg taaataattg tctgtaaata gggagaaatt     60
catggatcat caccctaatt cggtctttca ctcattttat catagacctg actaaagaac    120
ttggtcagag tttttactta tttaaaataa agaggacttc atggcatcca tgtgcaggta    180
cagctcccag aaaaaaaagc atgaaacacg agaggatcaa tagcattcga tctgaaacaa    240
aaggttgcag ctcaagactt tctccaaaat attaagatga tccaaagaat taccccaaga    300
tatccaacgt ataccaatgt gtataccgaa agtaagaaag ttcacgtgca ttctttgatt    360
tttctcccga gtgttctttt ctgaaatgag taaataagac tagaataaga gctaatgtat    420
ttttttteta aaaaaagttg aatgtggata caatatgatt atacattcat tagctatttt    480
aagtatattc tatttttttt ccccccaaaa gaacacaaat gtgttccgtc actttccatg    540
gagatcagat ctatcttaga attggacagg gtgcttatga tacaacttgt tcctatcaac    600
aactgcatgt tagacagcgc cgaatttaca gtcctactgg gcgccacttt tcaacccaca    660
tcatcaagat gaacaccacg ttatcttcat ccgctccaac cacatggtcc agcgccactg    720
gccaagaccg ccagccagcc aggccatcca acgtggtgca ttttctaaca ctccacgttc    780
gctgtacggc attatttctc cagccagaaa gaccgagaca gcgacgctgt tgggcgggcc    840
cgcggcctgc tctctctgct tccccatgag attcacgggc atcgctcctc gctcgtgcct    900
acgcgaccgc gccgatccac gtgacgtggc gcagcaatcg ttcttactag gcgcttgcac    960
gtgtcgttcg catgcgaagc gtccacactg ccaacgacct ccttaaatat ccttgtgata   1020
ttcgccttac gatctcacac ttcgcacgca aaggccagtc gcagatttgg gttgaatttg   1080
ctgcgttttg gcagattttg agcgagagat attagggaag                         1120
```

<210> SEQ ID NO 3
<211> LENGTH: 798
<212> TYPE: DNA
<213> ORGANISM: Xerophyta viscosa

<400> SEQUENCE: 3

```
atgaggaacg agggttttct gaaaatgaag accgacgttg gagtcgccga cgaggtgatc     60
tccggagatc tcaagcagct tggtgacgct gcaaagcggc tagctaaaca tgcgatcaag    120
ctcggcgcca gcttcggggt tggctctacc atagtccagg ctattgcttc gatcgctgct    180
atctatttgt tgatattgga ccggacaaac tggcgtacaa atatcttgac atcacttcta    240
attccatatg tttacttgag tcttccttca gtgatattca acctattcag gggcgacctg    300
ggcagatggc tttcattcat tggcgtagta atgaagctct tcttccaccg acacttccca    360
gttaccttgg aactgcttgt gtctctcatt ctcctgattg tggtttcccc cactttcatt    420
gcccacacaa tcagaggcag tctcattgga gtcttcatct tccttgtcat cgcctgctac    480
ctcctccaag agcacattag atcagctggt ggcttcaaaa acgcgttcac aaagagcaat    540
gggatttcaa acagcgtcgg gatcatcatt ctactgatcc acccgatctg gagcttggtg    600
gtgtatttcc tctacacgtc tttgctgcaa cttcttgcat actctccttc cccttgttgt    660
tgcatattat acaataagtg gtttaatttc atgcatgttt gtaaatgtgt aagccttcat    720
atgtattctc agtcaattgg gtcatgcgtg tccatatttt tcgtgcagtt tgtattcatc    780
tatgaagctg aattttaa                                                  798
```

-continued

<210> SEQ ID NO 4
<211> LENGTH: 489
<212> TYPE: DNA
<213> ORGANISM: Xerophyta viscosa

<400> SEQUENCE: 4

```
atggctccga tcgcagtcgg tgaaacgatc ccagacggaa cgctcggatg gttcgacgag     60

aaggacgagt tgaagcagat ctcgatccac tcgctcgccg ccggaaagaa gatcgtgctc    120

atcggtgtcc ccggcgcatt cactcctact tgcagtatgc aacacgttcc aagtttcatt    180

gagaaagcag aggagctgaa agctaagggc gttgatgagt tccttgttat tagtgttaat    240

gatcccttcg tgatgaaggc ttggtcgaaa acatatcctg agaacaagca tgtgaagttc    300

ctagccgatg gatcggggaa gtacacccaa gctcttggcg tggaactcga tctgtccgag    360

aaggggctcg ggctccgttc acggaggttt gctatccttg tagacgactt gaaggttaag    420

gttgcaaatg tcgaggaggg cggagcattt accatttcag gtgccgatga gatcttgaag    480

gcagtctag                                                            489
```

<210> SEQ ID NO 5
<211> LENGTH: 960
<212> TYPE: DNA
<213> ORGANISM: Xerophyta viscosa

<400> SEQUENCE: 5

```
atggcgcatg caccgtgttt tgctgatgcg aagacacaga gcttcaagct cctcagcggg     60

cactcaatcc ccgcagttgg gctcggcacg tggaagtctg gtgacaaggc cggcaacgcc    120

gtatacactg ccatcactga gggaggatac aggcacattg ataccgcagc acaatatgga    180

gtccatgaag aggtaggcaa tgctcttcaa tctgctttga aagcagggat caataggaag    240

gctttgttcg tcacatcgaa agtatggtgc gaagatttat cacctgaaag agttcgacct    300

gcattgaaaa atacacttga ggagctacaa ctggattacc ttgatctcta cctgattcac    360

tggcctatcc accttaaaaa gggcgcacac atgcctcctg aggctggtga ggtgctagag    420

ttcgacatag gaggagtgtg gagggaaatg gagaagctcg tcaaagtagg gcttgttaga    480

gatattggta tctctaactt cactgtgaag aaactcgaaa aacttctaaa ttttgctgaa    540

ataaagccct cggtgtgcca gatggagatg cacccgggtt ggagaaacga caagatgttt    600

gagatttgca ggaaatatgg tattcataca actgcttatt cacctctcgg atcttccgag    660

cgtgatctcc tcagtgatcc aactgttttg aagatagcaa acaagctcaa caagagccca    720

ggtcaacttc tggtgagatg ggctgttcaa agaggaacta gtgtcatccc aaaatcgacc    780

aacccggaga ggataaagga gaacatccag gtcttcgggt gggagattcc tgcagaggat    840

ttccagattt tgagcagcct tagtgaacag aagagagtct tggatggtga agatctcttc    900

gtcaacaaaa cccatggccc gttcaggagc gctgctgaac tctgggacgg tgaagtctaa    960
```

<210> SEQ ID NO 6
<211> LENGTH: 69
<212> TYPE: DNA
<213> ORGANISM: Foot and Mouth Disease Virus

<400> SEQUENCE: 6

```
ggcagtggac agctgttgaa ttttgacctt cttaaacttg cgggagacgt cgagtccaac     60

cctgggccc                                                             69
```

<210> SEQ ID NO 7

<211> LENGTH: 257
<212> TYPE: DNA
<213> ORGANISM: Agrobacterium tumefaciens

<400> SEQUENCE: 7
acccgatcgt tcaaacattt ggcaataaag tttcttaaga ttgaatcctg ttgccggtct 60
tgcgatgatt atcatataat ttctgttgaa ttacgttaag catgtaataa ttaacatgta 120
atgcatgacg ttatttatga gatgggtttt tatgattaga gtcccgcaat tatacattta 180
atacgcgata gaaaacaaaa tatagcgcgc aaactaggat aaattatcgc gcgcggtgtc 240
atctatgtta ctagatc 257

<210> SEQ ID NO 8
<211> LENGTH: 9189
<212> TYPE: DNA
<213> ORGANISM: Artificial Sequence
<220> FEATURE:
<223> OTHER INFORMATION: pTF101.1 vector

<400> SEQUENCE: 8
agtactttaa agtactttaa agtactttaa agtactttga tccaacccct ccgctgctat 60
agtgcagtcg gcttctgacg ttcagtgcag ccgtcttctg aaaacgacat gtcgcacaag 120
tcctaagtta cgcgacaggc tgccgccctg cccttttcct ggcgttttct tgtcgcgtgt 180
tttagtcgca taaagtagaa tacttgcgac tagaaccgga gacattacgc catgaacaag 240
agcgccgccg ctggcctgct gggctatgcc cgcgtcagca ccgacgacca ggacttgacc 300
aaccaacggg ccgaactgca cgcggccggc tgcaccaagc tgttttccga gaagatcacc 360
ggcaccaggc gcgaccgccc ggagctggcc aggatgcttg accacctacg ccctggcgac 420
gttgtgacag tgaccaggct agaccgcctg gcccgcagca cccgcgacct actggacatt 480
gccgagcgca tccaggaggc cggcgcgggc ctgcgtagcc tggcagagcc gtgggccgac 540
accaccacgc cggccggccg catggtgttg accgtgttcg ccggcattgc cgagttcgag 600
cgttccctaa tcatcgaccg cacccggagc gggcgcgagg ccgccaaggc ccgaggcgtg 660
aagtttggcc cccgccctac cctcaccccg gcacagatcg cgcacgcccg cgagctgatc 720
gaccaggaag gccgcaccgt gaaagaggcg gctgcactgc ttggcgtgca tcgctcgacc 780
ctgtaccgcg cacttgagcg cagcgaggaa gtgacgccca ccgaggccag gcggcgcggt 840
gccttccgtg aggacgcatt gaccgaggcc gacgccctgg cggccgccga gaatgaacgc 900
caagaggaac aagcatgaaa ccgcaccagg acggccagga cgaaccgttt ttcattaccg 960
aagagatcga ggcggagatg atcgcggccg ggtacgtgtt cgagccgccc gcgcacgtct 1020
caaccgtgcg gctgcatgaa atcctggccg gtttgtctga tgccaagctg gcggcctggc 1080
cggccagctt ggccgctgaa gaaaccgagc gccgccgtct aaaaaggtga tgtgtatttg 1140
agtaaaacag cttgcgtcat gcggtcgctg cgtatatgat gcgatgagta aataaacaaa 1200
tacgcaaggg gaacgcatga aggttatcgc tgtacttaac cagaaaggcg ggtcaggcaa 1260
gacgaccatc gcaacccatc tagcccgcgc cctgcaactc gccggggccg atgttctgtt 1320
agtcgattcc gatccccagg gcagtgcccg cgattgggcg gccgtgcggg aagatcaacc 1380
gctaaccgtt gtcggcatcg accgcccgac gattgaccgc gacgtgaagg ccatcggccg 1440
gcgcgacttc gtagtgatcg acggagcgcc ccaggcggcg gacttggctg tgtccgcgat 1500
caaggcagcc gacttcgtgc tgattccggt gcagccaagc ccttacgaca tatgggccac 1560
cgccgacctg gtggagctgg ttaagcagcg cattgaggtc acggatggaa ggctacaagc 1620

-continued

```
ggcctttgtc gtgtcgcggg cgatcaaagg cacgcgcatc ggcggtgagg ttgccgaggc   1680
gctggccggg tacgagctgc ccattcttga gtcccgtatc acgcagcgcg tgagctaccc   1740
aggcactgcc gccgccggca caaccgttct tgaatcagaa cccgagggcg acgctgcccg   1800
cgaggtccag gcgctggccg ctgaaattaa atcaaaactc atttgagtta atgaggtaaa   1860
gagaaaatga gcaaaagcac aaacacgcta agtgccggcc gtccgagcgc acgcagcagc   1920
aaggctgcaa cgttggccag cctggcagac acgccagcca tgaagcgggt caactttcag   1980
ttgccggcgg aggatcacac caagctgaag atgtacgcgg tacgccaagg caagaccatt   2040
accgagctgc tatctgaata catcgcgcag ctaccagagt aaatgagcaa atgaataaat   2100
gagtagatga attttagcgg ctaaaggagg cggcatggaa aatcaagaac aaccaggcac   2160
cgacgccgtg gaatgcccca tgtgtggagg aacgggcggt tggccaggcg taagcggctg   2220
ggttgtctgc cggccctgca atggcactgg aacccccaag cccgaggaat cggcgtgagc   2280
ggtcgcaaac catccggccc ggtacaaatc ggcgcggcgc tgggtgatga cctggtggag   2340
aagttgaagg ccgcgcaggc cgcccagcgg caacgcatcg aggcagaagc acgccccggt   2400
gaatcgtggc aagcggccgc tgatcgaatc cgcaaagaat cccggcaacc gccggcagcc   2460
ggtgcgccgt cgattaggaa gccgcccaag ggcgacgagc aaccagattt tttcgttccg   2520
atgctctatg acgtgggcac ccgcgatagt cgcagcatca tggacgtggc cgttttccgt   2580
ctgtcgaagc gtgaccgacg agctggcgag gtgatccgct acgagcttcc agacgggcac   2640
gtagaggttt ccgcagggcc ggccggcatg gccagtgtgt gggattacga cctggtactg   2700
atggcggttt cccatctaac cgaatccatg aaccgatacc gggaagggaa gggagacaag   2760
cccggccgcg tgttccgtcc acacgttgcg gacgtactca agttctgccg gcgagccgat   2820
ggcggaaagc agaaagacga cctggtagaa acctgcattc ggttaaacac cacgcacgtt   2880
gccatgcagc gtacgaagaa ggccaagaac ggccgcctgg tgacggtatc cgagggtgaa   2940
gccttgatta gccgctacaa gatcgtaaag agcgaaaccg ggcggccgga gtacatcgag   3000
atcgagctag ctgattggat gtaccgcgag atcacagaag gcaagaaccc ggacgtgctg   3060
acggttcacc ccgattactt tttgatcgat cccggcatcg gccgttttct ctaccgcctg   3120
gcacgccgcg ccgcaggcaa ggcagaagcc agatggttgt tcaagacgat ctacgaacgc   3180
agtggcagcg ccggagagtt caagaagttc tgtttcaccg tgcgcaagct gatcgggtca   3240
aatgacctgc cggagtacga tttgaaggag gaggcggggc aggctggccc gatcctagtc   3300
atgcgctacc gcaacctgat cgagggcgaa gcatccgccg gttcctaatg tacggagcag   3360
atgctagggc aaattgccct agcaggggaa aaaggtcgaa aaggtctctt tcctgtggat   3420
agcacgtaca ttgggaaccc aaagccgtac attgggaacc ggaacccgta cattgggaac   3480
ccaaagccgt acattgggaa ccggtcacac atgtaagtga ctgatataaa agagaaaaaa   3540
ggcgattttt ccgcctaaaa ctctttaaaa cttattaaaa ctcttaaaac ccgcctggcc   3600
tgtgcataac tgtctggcca gcgcacagcc gaagagctgc aaaaagcgcc tacccttcgg   3660
tcgctgcgct ccctacgccc cgccgcttcg cgtcggccta tcgcggccgc tggccgctca   3720
aaaatggctg gcctacggcc aggcaatcta ccagggcgcg gacaagccgc gccgtcgcca   3780
ctcgaccgcc ggcgcccaca tcaaggcacc ctgcctcgcg cgtttcggtg atgacggtga   3840
aaacctctga cacatgcagc tcccggagac ggtcacagct tgtctgtaag cggatgccgg   3900
gagcagacaa gcccgtcagg gcgcgtcagc gggtgttggc gggtgtcggg gcgcagccat   3960
```

-continued gacccagtca cgtagcgata gcggagtgta tactggctta actatgcggc atcagagcag 4020
attgtactga gagtgcacca tatgcggtgt gaaataccgc acagatgcgt aaggagaaaa 4080
taccgcatca ggcgctcttc cgcttcctcg ctcactgact cgctgcgctc ggtcgttcgg 4140
ctgcggcgag cggtatcagc tcactcaaag gcggtaatac ggttatccac agaatcaggg 4200
gataacgcag gaaagaacat gtgagcaaaa ggccagcaaa aggccaggaa ccgtaaaaag 4260
gccgcgttgc tggcgttttt ccataggctc cgcccccctg acgagcatca caaaaatcga 4320
cgctcaagtc agaggtggcg aaacccgaca ggactataaa gataccaggc gtttccccct 4380
ggaagctccc tcgtgcgctc tcctgttccg accctgccgc ttaccggata cctgtccgcc 4440
tttctccctt cgggaagcgt ggcgctttct catagctcac gctgtaggta tctcagttcg 4500
gtgtaggtcg ttcgctccaa gctgggctgt gtgcacgaac cccccgttca gcccgaccgc 4560
tgcgccttat ccggtaacta tcgtcttgag tccaacccgg taagacacga cttatcgcca 4620
ctggcagcag ccactggtaa caggattagc agagcgaggt atgtaggcgg tgctacagag 4680
ttcttgaagt ggtggcctaa ctacggctac actagaagga cagtatttgg tatctgcgct 4740
ctgctgaagc cagttacctt cggaaaaaga gttggtagct cttgatccgg caaacaaacc 4800
accgctggta gcggtggttt ttttgtttgc aagcagcaga ttacgcgcag aaaaaaagga 4860
tctcaagaag atcctttgat cttttctacg gggtctgacg ctcagtggaa cgaaaactca 4920
cgttaaggga ttttggtcat gcatgatata tctcccaatt tgtgtagggc ttattatgca 4980
cgcttaaaaa taataaaagc agacttgacc tgatagtttg gctgtgagca attatgtgct 5040
tagtgcatct aacgcttgag ttaagccgcg ccgcgaagcg gcgtcggctt gaacgaattt 5100
ctagctagac attatttgcc gactaccttg gtgatctcgc ctttcacgta gtggacaaat 5160
tcttccaact gatctgcgcg cgaggccaag cgatcttctt cttgtccaag ataagcctgt 5220
ctagcttcaa gtatgacggg ctgatactgg gccggcaggc gctccattgc ccagtcggca 5280
gcgacatcct tcggcgcgat tttgccggtt actgcgctgt accaaatgcg ggacaacgta 5340
agcactacat ttcgctcatc gccagcccag tcgggcggcg agttccatag cgttaaggtt 5400
tcatttagcg cctcaaatag atcctgttca ggaaccggat caaagagttc ctccgccgct 5460
ggacctacca aggcaacgct atgttctctt gcttttgtca gcaagatagc cagatcaatg 5520
tcgatcgtgg ctggctcgaa gatacctgca agaatgtcat tgcgctgcca ttctccaaat 5580
tgcagttcgc gcttagctgg ataacgccac ggaatgatgt cgtcgtgcac aacaatggtg 5640
acttctacag cgcggagaat ctcgctctct ccaggggaag ccgaagtttc caaaaggtcg 5700
ttgatcaaag ctcgccgcgt tgtttcatca agccttacgg tcaccgtaac cagcaaatca 5760
atatcactgt gtggcttcag gccgccatcc actgcggagc cgtacaaatg tacggccagc 5820
aacgtcggtt cgagatggcg ctcgatgacg ccaactacct ctgatagttg agtcgatact 5880
tcggcgatca ccgcttcccc catgatgttt aactttgttt tagggcgact gccctgctgc 5940
gtaacatcgt tgctgctcca taacatcaaa catcgaccca cggcgtaacg cgcttgctgc 6000
ttggatgccc gaggcataga ctgtacccca aaaaaacagt cataacaagc catgaaaacc 6060
gccactgcgc cgttaccacc gctgcgttcg gtcaaggttc tggaccagtt gcgtgacggc 6120
agttacgcta cttgcattac agcttacgaa ccgaacgagg cttatgtcca ctgggttcgt 6180
gcccgaattg atcacaggca gcaacgctct gtcatcgtta caatcaacat gctaccctcc 6240
gcgagatcat ccgtgtttca aacccggcag cttagttgcc gttcttccga atagcatcgg 6300
taacatgagc aaagtctgcc gccttacaac ggctctcccg ctgacgccgt cccggactga 6360

-continued

```
tgggctgcct gtatcgagtg gtgattttgt gccgagctgc cggtcgggga gctgttggct   6420
ggctggtggc aggatatatt gtggtgtaaa caaattgacg cttagacaac ttaataacac   6480
attgcggacg tttttaatgt actgaattaa cgccgaattg ctctagcatt cgccattcag   6540
gctgcgcaac tgttgggaag ggcgatcggt gcgggcctct tcgctattac gccagctggc   6600
gaaaggggga tgtgctgcaa ggcgattaag ttgggtaacg ccagggtttt cccagtcacg   6660
acgttgtaaa acgacggcca gtgccaagct aattcgcttc aagacgtgct caaatcacta   6720
tttccacacc cctatatttc tattgcactc ccttttaact gtttttttatt acaaaaatgc   6780
cctggaaaat gcactccctt tttgtgtttg tttttttgtg aaacgatgtt gtcaggtaat   6840
ttatttgtca gtctactatg gtggcccatt atattaatag caactgtcgg tccaatagac   6900
gacgtcgatt ttctgcattt gtttaaccac gtggatttta tgacatttta tattagttaa   6960
tttgtaaaac ctacccaatt aaagacctca tatgttctaa agactaatac ttaatgataa   7020
caattttctt ttagtgaaga aagggataat tagtaaatat ggaacaaggg cagaagattt   7080
attaaagccg cggtaagaga caacaagtag gtacgtggag tgtcttaggt gacttaccca   7140
cataacataa agtgacatta acaaacatag ctaatgctcc tatttgaata gtgcatatca   7200
gcatacctta ttacatatag ataggagcaa actctagcta gattgttgag cagatctcgg   7260
tgacgggcag gaccggacgg ggcggtaccg gcaggctgaa gtccagctgc cagaaaccca   7320
cgtcatgcca gttcccgtgc ttgaagccgg ccgcccgcag catgccgcgg ggggcatatc   7380
cgagcgcctc gtgcatgcgc acgctcgggt cgttgggcag cccgatgaca gcgaccacgc   7440
tcttgaagcc ctgtgcctcc agggacttca gcaggtgggt gtagagcgtg gagcccagtc   7500
ccgtccgctg gtggcggggg gagacgtaca cggtcgactc ggccgtccag tcgtaggcgt   7560
tgcgtgcctt ccaggggccc gcgtaggcga tgccggcgac ctcgccgtcc acctcggcga   7620
cgagccaggg atagcgctcc cgcagacgga cgaggtcgtc cgtccactcc tgcggttcct   7680
gcggctcggt acggaagttg accgtgcttg tctcgatgta gtggttgacg atggtgcaga   7740
ccgccggcat gtccgcctcg gtggcacggc ggatgtcggc cgggcgtcgt tctgggctca   7800
tggtagatcc cccgttcgta aatggtgaaa attttcagaa aattgctttt gctttaaaag   7860
aaatgattta aattgctgca atagaagtag aatgcttgat tgcttgagat tcgtttgttt   7920
tgtatatgtt gtgttgagaa ttaattctcg aggtcctctc caaatgaaat gaacttcctt   7980
atatagagga agggtcttgc gaaggatagt gggattgtgc gtcatccctt acgtcagtgg   8040
agatatcaca tcaatccact tgctttgaag acgtggttgg aacgtcttct ttttccacga   8100
tgctcctcgt gggtgggggt ccatctttgg gaccactgtc ggtagaggca tcttgaacga   8160
tagcctttcc tttatcgcaa tgatggcatt tgtaggagcc accttccttt tccactatct   8220
tcacaataaa gtgacagata gctgggcaat ggaatccgag gaggtttccg gatattaccc   8280
tttgttgaaa agtctcaatt gccctttggt cttctgagac tgtatctttg atatttttgg   8340
agtagacaag tgtgtcgtgc tccaccatgt tatcacatca atccacttgc tttgaagacg   8400
tggttggaac gtcttctttt tccacgatgc tcctcgtggg tgggggtcca tctttgggac   8460
cactgtcggc agaggcatct tcaacgatgg cctttccttt atcgcaatga tggcatttgt   8520
aggagccacc ttccttttcc actatcttca caataaagtg acagatagct gggcaatgga   8580
atccgaggag gtttccggat attacccttt gttgaaaagt ctcaattgcc ctttggtctt   8640
ctgagactgt atctttgata tttttggagt agacaagtgt gtcgtgctcc accatgttga   8700
```

-continued

```
cctgcaggca tgcaagcttg catgcctgca ggtcgactct agaggatccc cgggtaccga   8760

gctcgaattc gtaatcatgt catagctgtt tcctgtgtga aattgttatc cgctcacaat   8820

tccacacaac atacgagccg gaagcataaa gtgtaaagcc tggggtgcct aatgagtgag   8880

ctaactcaca ttaattgcgt tgcgctcact gcccgctttc cagtcgggaa acctgtcgtg   8940

ccagctgcat taatgaatcg gccaacgcgc ggggagaggc ggtttgcgta ttggagcttg   9000

agcttggatc agattgtcgt ttcccgcctt cagtttaaac tatcagtgtt tgacaggata   9060

tattggcggg taaacctaag agaaaagagc gtttattaga ataatcggat atttaaaagg   9120

gcgtgaaaag gtttatccgt tcgtccattt gtatgtgcat gccaaccaca gggttcccct   9180

cgggatcaa                                                           9189


<210> SEQ ID NO 9
<211> LENGTH: 265
<212> TYPE: PRT
<213> ORGANISM: Xerophyta viscosa

<400> SEQUENCE: 9

Met Arg Asn Glu Gly Phe Leu Lys Met Lys Thr Asp Val Gly Val Ala
1               5                   10                  15

Asp Glu Val Ile Ser Gly Asp Leu Lys Gln Leu Gly Asp Ala Ala Lys
            20                  25                  30

Arg Leu Ala Lys His Ala Ile Lys Leu Gly Ala Ser Phe Gly Val Gly
        35                  40                  45

Ser Thr Ile Val Gln Ala Ile Ala Ser Ile Ala Ala Ile Tyr Leu Leu
    50                  55                  60

Ile Leu Asp Arg Thr Asn Trp Arg Thr Asn Ile Leu Thr Ser Leu Leu
65                  70                  75                  80

Ile Pro Tyr Val Tyr Leu Ser Leu Pro Ser Val Ile Phe Asn Leu Phe
                85                  90                  95

Arg Gly Asp Leu Gly Arg Trp Leu Ser Phe Ile Gly Val Val Met Lys
            100                 105                 110

Leu Phe Phe His Arg His Phe Pro Val Thr Leu Glu Leu Leu Val Ser
        115                 120                 125

Leu Ile Leu Leu Ile Val Val Ser Pro Thr Phe Ile Ala His Thr Ile
    130                 135                 140

Arg Gly Ser Leu Ile Gly Val Phe Ile Phe Leu Val Ile Ala Cys Tyr
145                 150                 155                 160

Leu Leu Gln Glu His Ile Arg Ser Ala Gly Gly Phe Lys Asn Ala Phe
                165                 170                 175

Thr Lys Ser Asn Gly Ile Ser Asn Ser Val Gly Ile Ile Ile Leu Leu
            180                 185                 190

Ile His Pro Ile Trp Ser Leu Val Val Tyr Phe Leu Tyr Thr Ser Leu
        195                 200                 205

Leu Gln Leu Leu Ala Tyr Ser Pro Ser Pro Cys Cys Cys Ile Leu Tyr
    210                 215                 220

Asn Lys Trp Phe Asn Phe Met His Val Cys Lys Cys Val Ser Leu His
225                 230                 235                 240

Met Tyr Ser Gln Ser Ile Gly Ser Cys Val Ser Ile Phe Phe Val Gln
                245                 250                 255

Phe Val Phe Ile Tyr Glu Ala Glu Phe
            260                 265


<210> SEQ ID NO 10
```

<211> LENGTH: 162
<212> TYPE: PRT
<213> ORGANISM: Xerophyta viscosa

<400> SEQUENCE: 10

```
Met Ala Pro Ile Ala Val Gly Glu Thr Ile Pro Asp Gly Thr Leu Gly
1               5                   10                  15

Trp Phe Asp Glu Lys Asp Glu Leu Lys Gln Ile Ser Ile His Ser Leu
            20                  25                  30

Ala Ala Gly Lys Lys Ile Val Leu Ile Gly Val Pro Gly Ala Phe Thr
        35                  40                  45

Pro Thr Cys Ser Met Gln His Val Pro Ser Phe Ile Glu Lys Ala Glu
    50                  55                  60

Glu Leu Lys Ala Lys Gly Val Asp Glu Phe Leu Val Ile Ser Val Asn
65                  70                  75                  80

Asp Pro Phe Val Met Lys Ala Trp Ser Lys Thr Tyr Pro Glu Asn Lys
                85                  90                  95

His Val Lys Phe Leu Ala Asp Gly Ser Gly Lys Tyr Thr Gln Ala Leu
            100                 105                 110

Gly Val Glu Leu Asp Leu Ser Glu Lys Gly Leu Gly Leu Arg Ser Arg
        115                 120                 125

Arg Phe Ala Ile Leu Val Asp Asp Leu Lys Val Lys Val Ala Asn Val
    130                 135                 140

Glu Glu Gly Gly Ala Phe Thr Ile Ser Gly Ala Asp Glu Ile Leu Lys
145                 150                 155                 160

Ala Val
```

<210> SEQ ID NO 11
<211> LENGTH: 319
<212> TYPE: PRT
<213> ORGANISM: Xerophyta viscosa

<400> SEQUENCE: 11

```
Met Ala His Ala Pro Cys Phe Ala Asp Ala Lys Thr Gln Ser Phe Lys
1               5                   10                  15

Leu Leu Ser Gly His Ser Ile Pro Ala Val Gly Leu Gly Thr Trp Lys
            20                  25                  30

Ser Gly Asp Lys Ala Gly Asn Ala Val Tyr Thr Ala Ile Thr Glu Gly
        35                  40                  45

Gly Tyr Arg His Ile Asp Thr Ala Ala Gln Tyr Gly Val His Glu Glu
    50                  55                  60

Val Gly Asn Ala Leu Gln Ser Ala Leu Lys Ala Gly Ile Asn Arg Lys
65                  70                  75                  80

Ala Leu Phe Val Thr Ser Lys Val Trp Cys Glu Asp Leu Ser Pro Glu
                85                  90                  95

Arg Val Arg Pro Ala Leu Lys Asn Thr Leu Glu Glu Leu Gln Leu Asp
            100                 105                 110

Tyr Leu Asp Leu Tyr Leu Ile His Trp Pro Ile His Leu Lys Lys Gly
        115                 120                 125

Ala His Met Pro Pro Glu Ala Gly Glu Val Leu Glu Phe Asp Ile Gly
    130                 135                 140

Gly Val Trp Arg Glu Met Glu Lys Leu Val Lys Val Gly Leu Val Arg
145                 150                 155                 160

Asp Ile Gly Ile Ser Asn Phe Thr Val Lys Lys Leu Glu Lys Leu Leu
                165                 170                 175
```

```
Asn Phe Ala Glu Ile Lys Pro Ser Val Cys Gln Met Glu Met His Pro
            180                 185                 190

Gly Trp Arg Asn Asp Lys Met Phe Glu Ile Cys Arg Lys Tyr Gly Ile
        195                 200                 205

His Thr Thr Ala Tyr Ser Pro Leu Gly Ser Ser Glu Arg Asp Leu Leu
    210                 215                 220

Ser Asp Pro Thr Val Leu Lys Ile Ala Asn Lys Leu Asn Lys Ser Pro
225                 230                 235                 240

Gly Gln Leu Leu Val Arg Trp Ala Val Gln Arg Gly Thr Ser Val Ile
                245                 250                 255

Pro Lys Ser Thr Asn Pro Glu Arg Ile Lys Glu Asn Ile Gln Val Phe
            260                 265                 270

Gly Trp Glu Ile Pro Ala Glu Asp Phe Gln Ile Leu Ser Ser Leu Ser
        275                 280                 285

Glu Gln Lys Arg Val Leu Asp Gly Glu Asp Leu Phe Val Asn Lys Thr
    290                 295                 300

His Gly Pro Phe Arg Ser Ala Ala Glu Leu Trp Asp Gly Glu Val
305                 310                 315


<210> SEQ ID NO 12
<211> LENGTH: 23
<212> TYPE: PRT
<213> ORGANISM: Foot and Mouth Disease Virus

<400> SEQUENCE: 12

Gly Ser Gly Gln Leu Leu Asn Phe Asp Leu Leu Lys Leu Ala Gly Asp
1               5                   10                  15

Val Glu Ser Asn Pro Gly Pro
            20


<210> SEQ ID NO 13
<211> LENGTH: 23
<212> TYPE: DNA
<213> ORGANISM: Artificial Sequence
<220> FEATURE:
<223> OTHER INFORMATION: pSap1-RB F5 Oligonucleotide

<400> SEQUENCE: 13

tcgaatgcta ttgatcctgt cgt                                              23


<210> SEQ ID NO 14
<211> LENGTH: 21
<212> TYPE: DNA
<213> ORGANISM: Artificial Sequence
<220> FEATURE:
<223> OTHER INFORMATION: pSap1-RB R5 Oligonucleotide

<400> SEQUENCE: 14

agctcaagct ccaatacgca a                                                21


<210> SEQ ID NO 15
<211> LENGTH: 20
<212> TYPE: DNA
<213> ORGANISM: Artificial Sequence
<220> FEATURE:
<223> OTHER INFORMATION: Bar I-F Oligonucleotide

<400> SEQUENCE: 15

ggtctgcacc atcgtcaacc                                                  20


<210> SEQ ID NO 16
```

-continued

```
<211> LENGTH: 20
<212> TYPE: DNA
<213> ORGANISM: Artificial Sequence
<220> FEATURE:
<223> OTHER INFORMATION: Bar I-R Oligonucleotide

<400> SEQUENCE: 16

gtcatgccag ttcccgtgct                                                  20


<210> SEQ ID NO 17
<211> LENGTH: 17
<212> TYPE: DNA
<213> ORGANISM: Artificial sequence
<220> FEATURE:
<223> OTHER INFORMATION: M13F Oligonucleotide

<400> SEQUENCE: 17

gtaaaacgac ggccagt                                                     17


<210> SEQ ID NO 18
<211> LENGTH: 16
<212> TYPE: DNA
<213> ORGANISM: Artificial sequence
<220> FEATURE:
<223> OTHER INFORMATION: M13R Oligonucleotide

<400> SEQUENCE: 18

aacagctatg accatg                                                      16


<210> SEQ ID NO 19
<211> LENGTH: 28
<212> TYPE: DNA
<213> ORGANISM: Artificial sequence
<220> FEATURE:
<223> OTHER INFORMATION: XvSapI BclI F Oligonucleotide

<400> SEQUENCE: 19

atgatcaatg aggaacgagg gttttctg                                         28


<210> SEQ ID NO 20
<211> LENGTH: 25
<212> TYPE: DNA
<213> ORGANISM: Artificial sequence
<220> FEATURE:
<223> OTHER INFORMATION: XvPrx2 ClaI R Oligonucleotide

<400> SEQUENCE: 20

tatcgatgac tgccttcaag atctc                                            25


<210> SEQ ID NO 21
<211> LENGTH: 31
<212> TYPE: DNA
<213> ORGANISM: Artificial sequence
<220> FEATURE:
<223> OTHER INFORMATION: XvSapI ClaI R Oligonucleotide

<400> SEQUENCE: 21

tatcgataaa ctcagcctca tagatgaaga c                                     31
```

DROUGHT RESISTANCE MULTIGENE CONSTRUCT

BACKGROUND OF THE INVENTION

The present invention relates to a polygenic DNA construct consisting of three abiotic stress tolerance genes, separated by nucleic acids encoding FMDV 2A peptides under the control of a stress inducible promoter. The stable insertion of the construct into plants confers drought tolerance to the plants. The invention also provides for vectors, host cells, transgenic plants and transgenic seeds containing the construct.

The invention specifically relates to a polygenic DNA construct consisting of three genes from the plant Xerophyte viscose controlled by a stress inducible promoter. The stable insertion of the construct into plants has shown that transgenic plants containing the construct are more drought tolerant compared to the wild type plants which do not contain the construct.

Plant promoters play an important role in the process of plant gene expression and regulation. The use of constitutive promoters to drive gene expression in transgenic plants often results in stunted growth and reduction of yield. Accordingly, in order to prevent over-expression of genes of interest inducible promoters have significant advantages. Proteins expressed under the control of stress inducible promoters are only expressed when the plant is exposed to a stress.

Abiotic stresses include inter alia drought, salinity, cold and extreme temperatures. Drought has been the major cause of crop losses in agriculture. It is widely known that genes act together rather than in isolation in order to counteract the effects of dehydration due to water deficit in a plant. A need therefore exists for a number of genes to be switched on by a stress inducible promoter to counteract the effects of abiotic stress.

The stacking of multiple genes in plants has become an increasing area of study of modern plant research and biotechnology. Several methods have been used to stack genes into various plant genomes and then coordinate their expression. However, many of these strategies are unreliable because of the co-expression of the heterologous proteins.

The use of a self-processing viral 2A peptide bridge such as the Foot and Mouth Disease Virus 2A (FMDV 2A) polyprotein manipulates the ribosome to skip the synthesis of the glycyl-prolyl peptide bond at its C terminus leading to the release of the nascent protein and allowing translation of the downstream sequence. The FMDV 2A oligopeptide is only 23 amino acids (aa) long. The FMDV 2A oligopeptide comprises the following amino acid sequence GSGQLLNFDLLKLAGDVESNPGP (SEQ ID NO:12) and has a co-translational cleavage at its C terminus and a post translational cleavage at its N terminus mediated by the virus encoded proteinase.

SUMMARY OF THE INVENTION

The present invention relates to a polygenic DNA construct consisting of three abiotic stress tolerance genes, separated by nucleic acids encoding FMDV 2A peptides under the control of a stress inducible promoter. The stable insertion of the construct into plants confers drought tolerance to the plants. The invention also provides for vectors, host cells, transgenic plants and transgenic seeds containing the construct.

According to a first aspect of the invention there is provided for a recombinant nucleic acid molecule comprising a polygenic nucleic acid construct operably linked to an abiotic stress inducible promoter. The polygenic nucleic acid construct comprises: a nucleotide sequence encoding a Xvsap1 polypeptide, a nucleotide sequence encoding a first 2A element peptide, a nucleotide sequence encoding a XvAld polypeptide, a nucleotide sequence encoding a second 2A element peptide, a nucleotide sequence encoding a XvPrx2 polypeptide, and a terminator.

In one embodiment of the invention the first and second 2A element peptides are Foot-and-Mouth disease virus 2A element peptides.

In another embodiment of the invention the abiotic stress may be selected from the group consisting of osmotic stress, dehydration stress, temperature stress, drought, salinity and desiccation.

In a second aspect of the invention the polygenic nucleic acid construct comprises a nucleotide sequence encoding a first polypeptide of interest, a nucleotide sequence encoding a first 2A element peptide, nucleotide sequence encoding a second polypeptide of interest, a nucleotide sequence encoding a second 2A element peptide, a nucleotide sequence encoding a third polypeptide of interest, and a terminator. In this aspect of the invention the abiotic stress inducible promoter comprises a sequence of SEQ ID NO:2.

In one embodiment of the invention the polygenic nucleic acid construct comprises a sequence of SEQ ID NO:1.

In another embodiment of the invention the first, second and third polypeptides of interest are abiotic stress tolerance polypeptides. The abiotic stress tolerance peptides may be selected from the group consisting of XvSap1, XvPrx2 and XvAld.

In a third aspect of the invention there is provided for a vector comprising a recombinant nucleic acid molecule of the invention.

A forth aspect of the invention provides for a host cell transformed with the vector of the present invention. Preferably the host cell is a plant cell.

In one embodiment of the invention the host cell is stably transformed with the recombinant nucleic acid molecule of the invention. Those of skill in the art will however appreciate that it will be possible to also transiently express the recombinant nucleic acid molecule of the invention.

In yet another aspect of the invention there is provided for a transgenic plant comprising the recombinant nucleic acid molecule of the invention or the host cell as described herein.

The transgenic plant may be selected from the group consisting of alfalfa, barley, canola, cassava, cotton, maize, oats, rye, sorghum, soybean, sunflower, sweet potato, tobacco and wheat.

The invention also provides for a transgenic seed comprising the recombinant nucleic acid molecule the invention.

A further aspect of the invention provides for a method of producing an abiotic stress tolerant transgenic plant, the method comprising obtaining a recombinant nucleic acid molecule as described herein and stably transforming a plant with the recombinant nucleic acid molecule.

BRIEF DESCRIPTION OF THE FIGURES

Non-limiting embodiments of the invention will now be described by way of example only and with reference to the following figures.

SEQUENCE LISTING

Figure 1:
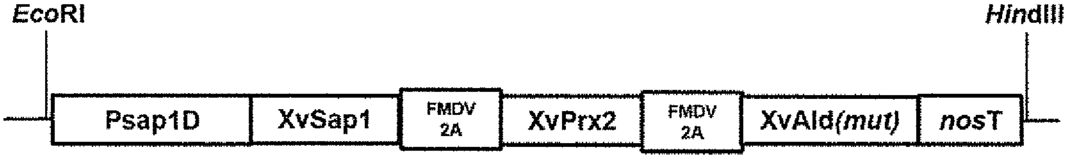
FIG. 1: Schematic illustration of the polygenic DNA construct in the plant transformation vector pTF101.1.

The nucleic acid and amino acid sequences listed in the accompanying sequence listing are shown using standard letter abbreviations for nucleotide bases, and the standard three letter abbreviations for amino acids. It will be understood by those of skill in the art that only one strand of each nucleic acid sequence is shown, but that the complementary strand is included by any reference to the displayed strand. In the accompanying sequence listing:

SEQ ID NO:1—Complete nucleotide sequence of polygenic DNA construct (3792 bp)

SEQ ID NO:2—Nucleotide sequence of truncated promoter Psap1D (1120 bp)

SEQ ID NO:3—Nucleotide sequence of XvSap1 gene (798 bp)

SEQ ID NO:4—Nucleotide sequence of XvPrx2 gene (489 bp)

SEQ ID NO:5—Nucleotide sequence of XvAldmut2 gene (960 bp)

SEQ ID NO:6—Nucleotide sequence of FMDV 2A region (69 bp)

SEQ ID NO:7—Nucleotide sequence of nosT terminator (257 bp)

SEQ ID NO:8—Nucleotide sequence of the pTF101.1 vector

SEQ ID NO:9—Amino acid sequence of XvSap1 polypeptide

SEQ ID NO:10—Amino acid sequence of XvPrx2 polypeptide

SEQ ID NO:11—Amino acid sequence of XvAldmut2 polypeptide

SEQ ID NO:12—Amino acid sequence of the FMDV 2A linker

SEQ ID NO:13—Nucleotide sequence of the Psap1-RB F5 oligonucleotide primer

SEQ ID NO:14—Nucleotide sequence of the Psap1-RB R5 oligonucleotide primer

SEQ ID NO:15—Nucleotide sequence of the Bar I-F oligonucleotide primer

SEQ ID NO:16—Nucleotide sequence of the Bar I-R oligonucleotide primer

SEQ ID NO:17—Nucleotide sequence of the M13F oligonucleotide primer

SEQ ID NO:18—Nucleotide sequence of the M13R oligonucleotide primer

SEQ ID NO:19—Nucleotide sequence of the XvSap1 Bcl F oligonucleotide primer

SEQ ID NO:20—Nucleotide sequence of the XvPrx2 Clal R oligonucleotide primer

SEQ ID NO:21—Nucleotide sequence of the XvSap1 Clal R oligonucleotide primer

DETAILED DESCRIPTION OF THE INVENTION

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

This invention relates to the production of a transgenic plant incorporating three genes separated by a nucleic acid sequence encoding the FMDV 2A peptide and regulated by a stress-inducible promoter, hereinafter referred to as the polygenic DNA construct (FIG. 1, (SEQ ID NO:1)). The FMDV 2A sequence contains a cleavage site so that upon translation each protein is expressed individually and not as one continuous fusion polypeptide. This is advantageous as a single polygenic nucleic acid construct is provided which encodes each of the three polypeptides of interest. Accordingly, each protein encoded by the polygenic DNA construct will be expressed as an individual polypeptide and functions separately and provides the desired protection to the cells upon exposure to an abiotic stress. The transgenic plant displays enhanced tolerance to drought stress due to the concerted expression of the transgenes under water limiting conditions. Furthermore, the transgenic plant does not demonstrate any adverse growth characteristics due to the fact that the promoter is stress-inducible, which ensures that the heterologous polypeptides are only produced when required.

It will be appreciated that the polynucleotides for minimal promoter (Psap1D), the stacked genes namely, XvSap1, XvPrx2, XvAldmut2, the FMDV 2A element and the nos terminator (nosT) may be artificially synthesised.

The polynucleotide of the present invention comprises a polygenic expression cassette which includes an abiotic stress-inducible promoter, a first gene of interest, a 2A element, a second gene of interest, a second 2A element, a third gene of interest and a terminator.

The terms "nucleic acid", "nucleic acid molecule" or "polynucleotide" encompass both ribonucleotides (RNA) and deoxyribonucleotides (DNA), including cDNA, genomic DNA, and synthetic DNA. The nucleic acid may be double-stranded or single-stranded. Where the nucleic acid is single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. By "RNA" is meant a sequence of two or more covalently bonded, naturally occurring or modified ribonucleotides. The term "DNA" refers to a sequence of two or more covalently bonded, naturally occurring or modified deoxyribonucleotides.

A "polycistronic expression cassette" as used herein refers to a polycistronic expression unit comprising nucleic acid molecules encoding more than one polypeptide of interest for the simultaneous and coordinated expression of the more than one polypeptide of interest in response to an abiotic stress. The abiotic-stress inducible promoter allows for the simultaneous transcription of the more than one gene of interest, as well as the FMDV 2A peptide. The cleavage of the more than one polypeptide of interest occurs at the 2A peptide sequence during translation.

The promoter of the polycistronic expression cassette includes signals for DNA or RNA dependent RNA polymerase binding and transcription initiation. The promoter is an abiotic stress inducible promoter. Those of skill in the art will appreciate that the activity on an inducible promoter increases or decreases in response to a signal, which in the present invention is an abiotic stress, such as, osmotic stress, dehydration stress, temperature stress, drought, salinity or desiccation.

The term "gene of interest" refers to a polynucleotide sequence, of any, length that encodes a gene product of interest, i.e. the protein, polypeptide or polynucleotide of interest. The gene of interest is a heterologous gene with respect to the host cell. The selected sequence can be a full length or a truncated gene, a fusion or tagged gene and can be a cDNA, a genomic DNA, or a DNA fragment, preferably, a cDNA.

A "protein," "peptide" or "polypeptide" is any chain of two or more amino acids, including naturally occurring or non-naturally occurring amino acids or amino acid analogues, irrespective of post-translational modification (e.g., glycosylation or phosphorylation).

A "host cell" refers to a cell into which the polycistronic expression cassette and its promoter are introduced. The term host cell includes both prokaryotic cells used for propagation of the construct to prepare vector stocks, and eukaryotic cells for expression of the polypeptides of interest, such as plant cells.

The term "complementary" refers to two nucleic acids molecules, e.g., DNA or RNA, which are capable of forming Watson-Crick base pairs to produce a region of double-strandedness between the two nucleic acid molecules. It will be appreciated by those of skill in the art that each nucleotide in a nucleic acid molecule need not form a matched Watson-Crick base pair with a nucleotide in an opposing complementary strand to form a duplex. One nucleic acid molecule is thus "complementary" to a second nucleic acid molecule if it hybridizes, under conditions of high stringency, with the second nucleic acid molecule. A nucleic acid molecule according to the invention includes both complementary molecules.

As used herein a "substantially identical" sequence is an amino acid or nucleotide sequence that differs from a reference sequence only by one or more conservative substitutions, or by one or more non-conservative substitutions, deletions, or insertions located at positions of the sequence that do not destroy or substantially reduce the antigenicity of one or more of the expressed polypeptides or of the polypeptides encoded by the nucleic acid molecules. Alignment for purposes of determining percent sequence identity can be achieved in various ways that are within the knowledge of those with skill in the art. These include using, for instance, computer software such as ALIGN, Megalign (DNASTAR), CLUSTALW or BLAST software. Those skilled in the art can readily determine appropriate parameters for measuring alignment, including any algorithms needed to achieve maximal alignment over the full length of the sequences being compared. In one embodiment of the invention there is provided for a polypeptide or polynucleotide sequence that has at least about 80% sequence identity, at least about 90% sequence identity, or even greater sequence identity, such as about 95%, about 96%, about 97%, about 98% or about 99% sequence identity to the sequences described herein.

Alternatively, or additionally, two nucleic acid sequences may be "substantially identical" if they hybridize under high stringency conditions. The "stringency" of a hybridisation reaction is readily determinable by one of ordinary skill in the art, and generally is an empirical calculation which depends upon probe length, washing temperature, and salt concentration. In general, longer probes required higher temperatures for proper annealing, while shorter probes require lower temperatures. Hybridisation generally depends on the ability of denatured DNA to re-anneal when complementary strands are present in an environment below their melting temperature. A typical example of such "stringent" hybridisation conditions would be hybridisation carried out for 18 hours at 65° C. with gentle shaking, a first wash for 12 min at 65° C. in Wash Buffer A (0.5% SDS; 2×SSC), and a second wash for 10 min at 65° C. in Wash Buffer B (0.1% SDS; 0.5% SSC).

In some embodiments, the nucleic acid molecules of the invention are operably linked to other sequences. By "operably linked" is meant that the nucleic acid molecules encoding the XvSap1 (SEQ ID NO:9), XvPrx2 (SEQ ID NO:10) and XvAldmut2 (SEQ ID NO:11) polypeptides or FMDV 2A (SEQ 1D NO:12) peptides described herein and regulatory sequences are connected in such a way as to permit expression of the proteins of interest when the appropriate molecules are bound to the regulatory sequences. Such operably linked sequences may be contained in vectors or expression constructs which can be transformed or transfected into host cells for expression. It will be appreciated that expression of the proteins of interest will occur in response to an abiotic stress.

The nucleic acid molecules of the invention include the XvSap1 gene (SEQ ID NO:3), the XvPrx2 gene (SEQ ID NO:4) and the XvAldmut2 gene (SEQ ID NO:5), the aforementioned genes are separated by a FMDV 2A linker (SEQ ID NO:6).

XvSap1 is a stress associated protein isolated from a cDNA library synthesized from dehydration stressed Xerophytha viscose leaves. The XvSap1 protein (SEQ ID NO:9) is highly hydrophobic and possesses two membrane lipoprotein lipid attachment sites. These features suggest that XvSap1 is anchored within the plasma membrane. It displays high sequence similarity with G-protein coupled receptors and consequently is postulated to play a signalling role during abiotic stress. The amino acid sequence of XvSap1 displayed 49% identity to WCOR413 from wheat (renamed TacCOR413-PM). This family of stress inducible proteins consist of two distinct groups based on their intracellular localisation, COR413 plasma membrane (COR413-PM) proteins and COR413 thylakoid (COR413-TM) proteins. The COR413 protein family has not been identified in other eukaryotic or prokaryotic databases suggesting that it is unique to the plant kingdom. Expression of XvSap1 in *Escherichia* co/i cells conferred osmotic stress tolerance when the cells were grown in 1 M sorbitol. Transgenic *Arabidopsis* thaliana and *Nicotiana tabacum* plants constitutively expressing XvSap1 showed increase tolerance to osmotic, salt, heat and dehydration stress. These features suggest that XvSap1 could play an important role in repair of damage to the cell membrane.

XvPrx2, encodes a type II Prx, the XvPrx2 protein (SEQ ID NO:10) was isolated from Xerophyte viscose from a low temperature stress library. The Prx's are a family of multifunctional antioxidant thiol-dependent peroxidases that have been identified to be ubiquitous in most organisms. This diversity is reflected in slight evolutionary modifications in sequence and structure built around a common peroxidatic active site. The major functions of Prx's comprise cellular protection against oxidative stress, modulation of intracellular signalling cascades that apply $H_2O_2$ as a second messenger molecule and regulation of cell proliferation. The accumulation of these toxic compounds in plant cells especially reactive oxygen/nitrogen species can cause cell death which is detrimental to the plant. The XvPrx2 protein was determined to be a cytosol localised, stress inducible antioxidant enzyme involved in the protection of nucleic acids by scavenging reactive oxygen species. Besides these characteristics, two further characteristics of this protein are of significance. The first is the discovery that multiple XvPrx2 homologues exist in X. viscose. The second is that the XvPrx2 protein is atypical in that it possesses a single cysteine only.

The XvAldmut2 gene was isolated from a Xerophyte viscose dehydration library and encodes for an aldose reductase, which catalyses the reduction of sugars to their analogous alcohol. It has also been demonstrated that plant aldose reductase can detoxify cytotoxic aldehydes, such as 4-hydroxynon-2-enal that is a product of ROS-induced lipid peroxidation. Transcript and protein levels of XvAldmut2 (SEQ ID NO:11) have been shown to increase within leaves in response to water deficit.

The term "recombinant" means that something has been recombined. When used with reference to a nucleic acid construct the term refers to a molecule that comprises nucleic acid sequences that are joined together or produced by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Accordingly, a recombinant nucleic acid construct indicates that the nucleic acid molecule has been manipulated using genetic engineering, i.e. by human intervention. Recombinant nucleic acid constructs may be introduced into a host cell by transformation.

The term "2A" or "2A element" refers to an about 18-24 amino acid sequence, which can be found in picornaviruses, such as Foot-and-Mouth Disease Virus. A highly conserved consensus motif at the C-terminus of the 2A element mediates cleavage between the C-terminal glycine and the N-terminal proline. This "cleavage" does not require any additional factors like proteases (Szymczak et al (2005)) and allows for polycistronic transcription of genes of interest with resultant cleavage of the translated polypeptides into separate proteins. Those of skill in the art will appreciate that when a FMDV 2A element is operably linked to a first gene and a second gene is operably linked to the 2A element, then the 2A element facilitates the co-translational "cleavage" of the expressed polypeptides into separate proteins. The 2A element thus allows multiple proteins to be encoded as a single polyprotein, which dissociate into component proteins on translation. The 2A peptide sequence impairs normal peptide bond formation through a mechanism of ribosomal skipping.

The term "vector" refers to a means by which polynucleotides or gene sequences can be introduced into a cell. There are various types of vectors known in the art including plasmids, viruses, bacteriophages and cosmids. Generally polynucleotides or gene sequences are introduced into a vector by means of a cassette. The term "cassette" refers to a polynucleotide or gene sequence that is expressed from a vector, for example, the polynucleotide or gene sequence encoding the XvSap1, XvPrx2 and XvAld polypeptides and the FMDV 2A peptides. It will be appreciated in the present invention that the cassette provides regulatory sequences in the form of an abiotic stress inducible promoter and a terminator. "Regulatory sequences" include but are not limited to promoters, transcription termination sequences, enhancers, splice acceptors, donor sequences, introns, ribosome binding sequences, poly(A) addition sequences, and/or origins of replication.

The current invention provides a specific combination of a stress-inducible promoter and three stress inducible genes isolated from Xerophyte viscose, where each gene is separated by a 69 bp FMDV 2A nucleotide sequence.

Various combinations of stress inducible genes, operably linked to the XvPsap1D promoter (SEQ ID NO:2) and nosT terminator (SEQ ID NO:7) and individually separated by the FMDV 2A linker sequence were evaluated under drought stress conditions. The combination XvSap1::FMDV2A::XvPrx2:: FMDV2A::XvAldmut2::nosT under control of the minimal stress inducible promoter (XvPsap1D (SEQ ID NO:2); as described in WO 2014/037919) displayed the highest levels of tolerance to drought.

The following example is offered by way of illustration and not by way of limitation.

Example

Cloning of the polygenic DNA construct into pTF101.1:: Psap1D recombinant vector The XvSap1::FMDV2A::XvPrx2::FMDV2A::XvAldmut2::nosT construct was synthesised de nova incorporating a Bell site at the 5' end as well as a HindIII site at the 3' site of the construct. Plasmid isolation was carried out on the synthesised construct from the pUC57 plasmid. The synthesised product was then digested, electrophoresed and excised from the gel and purified.

The polygenic DNA construct (SEQ ID NO:1) without the minimal promoter was cloned into the pDrive (Qiagen, USA) vector by digesting both the vector as well as the polygenic DNA construct with BclI and HindIII restriction enzymes at 37° C. for 1 hour. The digested products where ligated to form the recombinant pDrive plasmid (pDrive:: XvSap1::FMDV2A::XvPrx2::FMDV2A::XvAldmut2:: nosT). The recombinant plasmid was transformed into *E. coli* DH5α cells and colony PCR was performed to identify positively transformed clones. Colony PCR was performed using two primer sets M13 F (−20) having the sequence GTA AAA CGA CGG CCA GT (SEQ ID NO:17) and M13 R (−20) having the sequence MC AGC TAT GAC CAT G (SEQ ID NO:18) as well as XvSap1 BclI F having the sequence ATG ATC AAT GAG GM CGA GGG TTT TCT G (SEQ ID NO:19) and XvPrx2 C/al R having the sequence TAT CGA TGA CTG CCT TCA AGA TCT C (SEQ ID NO:20). These primer sets amplified a 2500 bp as well as 1401 bp fragment, respectively. The following PCR conditions were used for the amplifications for both primer sets: 94° C. for 5 min; 30 cycles of 94° C. for 30 s, 54° C. for 45 s, 72° C. for 90 s; and a final extension of 72° C. for 10 min.

The polygenic NA construct was then cloned into pTF101.1 vector (SEQ ID NO:8) containing the minimal Psap1D promoter by digesting the pDrive polygenic DNA construct with BO and HindIII restriction enzymes and the pTF101.1 vector containing the minimal Psap1D promoter with BamHI and HindIII. It should be noted that BclI and BamHI have compatible cohesive ends and can therefore ligate. The polygenic DNA construct was ligated to pTF101.1::Psap1D digested ends to form the recombinant pTF101.1 plasmid (pTF101.1::Psap1D::XvSap1: FMDV2A::XvPrx2:: FMDV2A::XvAldmut2::nosT) (FIG.

1). The recombinant plasmid was transformed into *E. coli* DH5α cells and colony PCR was performed using XvSap1 specific primers (XvSapl BclI F (SEQ ID NO:19) and XvSap1 Dal R having the sequence TAT CGA TM ACT CAG CCT CAT AGA TGA AGA C (SEQ ID NO:21).under the following conditions: 95° C. for 10 min; 30 cycles of 95° C. for 30 s, 54° C. for 45 s, 72° C. for 60 s and a final extension of 72° C. for 10 min in order to identify positively transformed clones. An EcoRI and HindIII restriction enzyme digest was performed to release the entire insert (Psap1D::XvSap1::FMDV2A::XvAldmut::nosT) and the size was verified on an ethidium bromide stained agarose gel.

Transformation of *Agrobacterium tumefaciens*

The recombinant pTF101.1 construct was transformed into competent *A. tumefaciens* EHA101 cells. Following transformation and growth of *A. tumefaciens* cells, colony PCR was performed to identify positively transformed clones. The presence of the polygenic DNA construct was determined by PCR amplification of part of the minimal Psap1D promoter fragment as well as part of the T-DNA RB region using a promoter-specific forward primer: pSap1-RB F5 having the sequence TOG AAT GCT ATT GAT CCT GTC GT (SEQ ID NO:13) and a T-DNA right border specific reverse primer: pSap1-RB R5 having the sequence AGO TCA AGC TCC AAT ACG CAA (SEQ ID NO:14). Amplification of the 449 bp fragment was carried out under the following PCR conditions: 95° C. for 5 min; 35 cycles of 95° C. for 30 s, 54° C. for 30 s, 72° C. for 30 s; and a final extension of 72° C. for 10 min.

Plant Transformation and Selection

Wild type *N. tabacum* (SR1 ecotype) seed was sterilised and germinated on sterile potting soil mix. Plants were cultured in the growth room with set conditions (24° C.; 16 h light, 8 h dark).

Four to six inch leaves were selected from 2 month old plants. Leaves were soaked in sterile water for 30 min and sterilised. Sterile leaves were sliced into uniform segments of 5 mm avoiding the leaf margins and mid vein. Leaf explants were placed adaxial side up onto pre-culture media.

One millilitre of a 16 h culture of *A. tumefaciens* carrying the polycistronic multigene construct was inoculated into 200 ml of YEP media supplemented with the appropriate antibiotics. The cultures were incubated at 30° C. until an absorbance reading of approximately 0.8 at 600 nm was obtained. The cultures were centrifuged for 20 min at 6000×g at 4° C. The supernatant was discarded and the bacterial pellets re-suspended in 50 ml of liquid co-cultivation media.

Leaf discs were infected for 30 min in the dark with the *Agrobacterium* inoculum containing the polygenic DNA construct in sterile petri dishes. The petri dish was agitated once every 10 min. Thereafter, infected leaf discs were blot dried on sterile filter paper. Each infected explant was transferred to co-cultivation medium and incubated for 3 days at 23° C. (18 h light, 6 h dark; light intensity of 140 $\mu mol/m^2/s$). The adaxial part of the leaf was kept in contact with the medium.

Following the 3 day co-cultivation period, leaf discs were selected on shooting medium. Leaf explants were placed under an 18 h light regime with light intensity of 140 $\mu mol/m^2/s$ at 28° C. Putative transformants were sub-cultured fortnightly onto fresh media until sizable shoots were formed. BASTA resistant shoots were selected, excised and transferred to rooting media.

Putative transformants with well-established root systems were transferred to pots containing sterile potting soil and cultured with set conditions. The plants were covered with Saran Wrap® for 8 days to assist acclimatisation and minimise dehydration. Once acclimatised, the putative transformants were transferred to 6 inch pots containing potting soil under normal growth conditions. Mature plants were self-pollinated and seed was harvested from mature dry pods.

Putative transgenic tobacco seed was sterilised and germinated on MS media supplemented with 8 g/l agar and 3 mg/ml BASTA. Plants were cultured in the growth room with set conditions (24° C.; 16 h day, 8 h night). The surviving BASTA resistant plants with well-established root systems were transferred to trays containing 0.1 g/l Gaucho SW treated potting soil and covered with Saran Wrap® for 1 week. Three weeks later, BASTA resistant transgenic plants were transferred to pots containing potting soil.

Leaves were sampled from putative transgenic plants and were flash frozen in liquid nitrogen. Genomic DNA was extracted using the Dellaporta extraction protocol. The presence of the polygenic DNA construct was determined by PCR amplification with the Psap1-RB F5 (SEQ ID NO:13) and Psap1-RB R5 (SEQ ID NO:14) primer pair. The bar gene (421 bp) was also amplified using the following PCR conditions (95° C. for 10 min; 35 cycles of 95° C. for 30 s, 54° C. for 30 s, 72° C. for 30 s; and a final extension of 72° C. for 5 min) and using the bar gene specific primers: Bar 1-F GGT CTG CAC CAT CGT CAA CC (SEQ ID NO:15) and Bar I-R GTC ATG CCA GTT CCC GTG CT (SEQ ID NO:16).

Dehydration and Rehydration of Transgenic Plants

The first dehydration/rehydration treatments were carried out in a Percival® chamber and the second dehydration/rehydration treatment was carried out in a Conviron® chamber.

Prior to the first dehydration/rehydration treatment, plants were transferred to pots containing set amounts of soil and water. Plants were moved to the Percival® chamber (Percival® Intellus control system) and incubated under set conditions (26° C.; 16 h day, 8 h night; 60% humidity; light intensity of 100 $\mu mol/m^2/s$) for 1 week to acclimatise. Dehydration stress was carried out on whole plants and achieved by withholding water for a period of seven days and then rehydrating the plants for a further five days.

Prior to the second dehydration/rehydration treatment, whole mature plants were transferred to pots containing set amounts of soil and water. Plants were moved to the Conviron® chamber and incubated under set conditions (26° C.; 16 h day, 8 h night; 60% humidity; light intensity of 100 $\mu mol/m^2/s$) for 1 week to acclimatise. Dehydration stress was carried out on whole plants and achieved by withholding water for a period of ten days and rehydrating the plants for a further four days. Throughout the dehydration period, flowers and seed pods were counted on day one and day ten of dehydration, prior to rehydration. Rehydration was initiated on day ten after the flowers and pods were counted. Rehydration lasted four days and the total biomass of the transgenic plants was measured on day four of the rehydration.

Dehydration and Rehydration Treatment of Transgenic *N. tabacum* Plants

Figure 2:
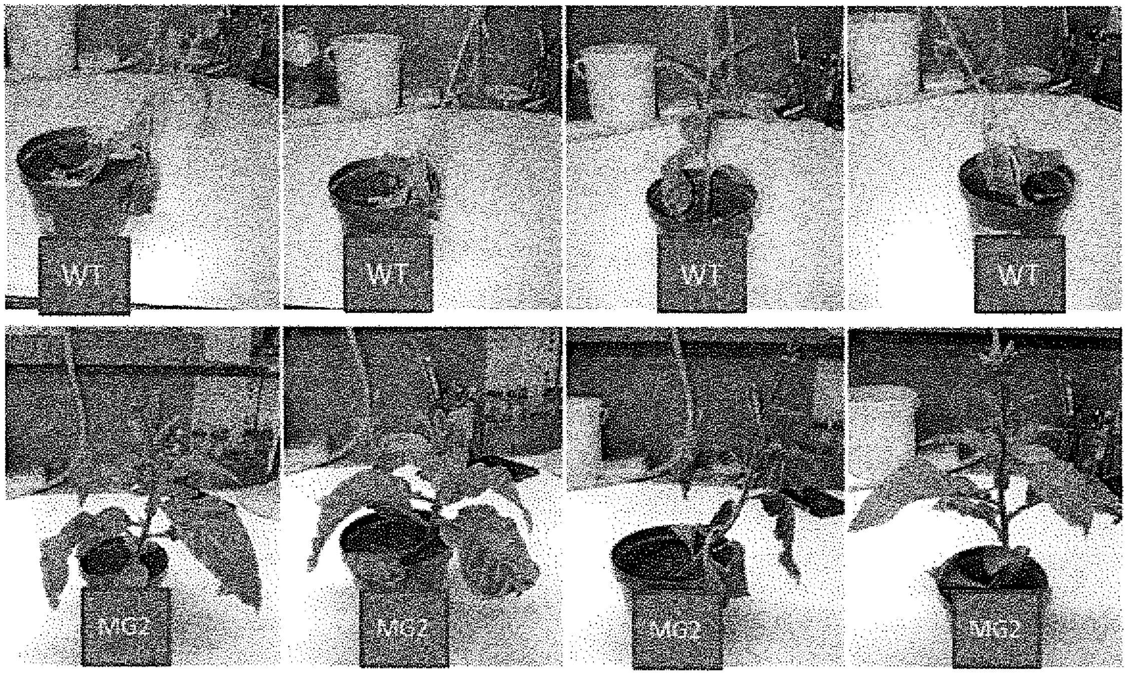
FIG. 2: Photos of 4 replicates of the wild-type (upper set) and transgenic plants (lowers set; MG2), respectively. These were dehydrated for seven days and then tested for recovery by rehydrating the plants for five days.

The first dehydration and rehydration treatments on wild type (WT) tobacco had a major impact on the overall morphology of the plant. In the absence of the polygenic DNA construct the leaves look withered and close to dying when compared to the transgenic lines containing the polygenic DNA construct (FIG. 2). The transgenic plants also had leaves that looked fuller and bigger and appeared to have a minor response to the stress. On the other hand the wild type control plants were severely affected following the stress treatment.

Figure 3:
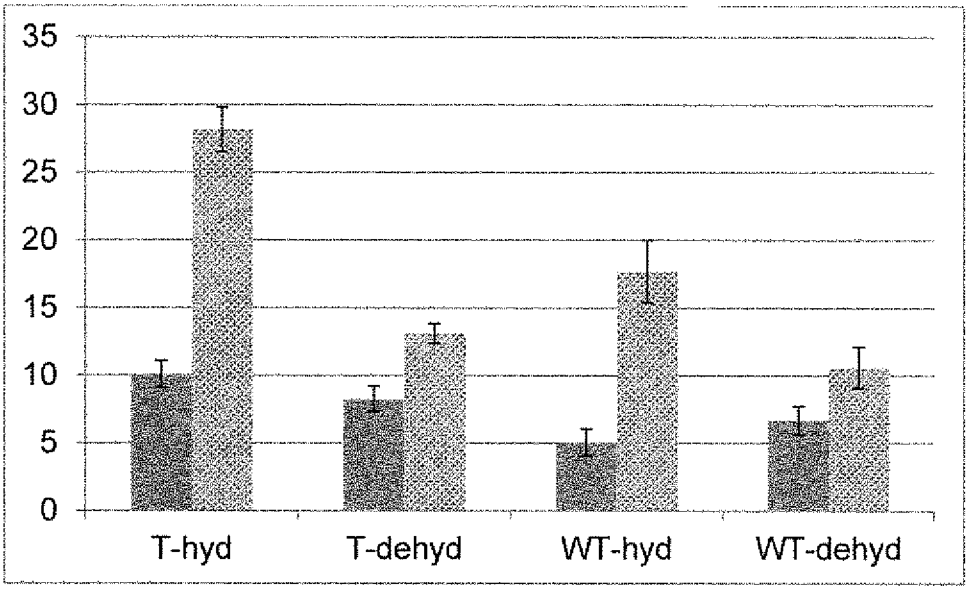
FIG. 3: The effect of dehydration on seed pod formation of WT and transgenic plants. The bars reflect a shift in pod formation over a 11 day period in mature plants.
Figure 4:
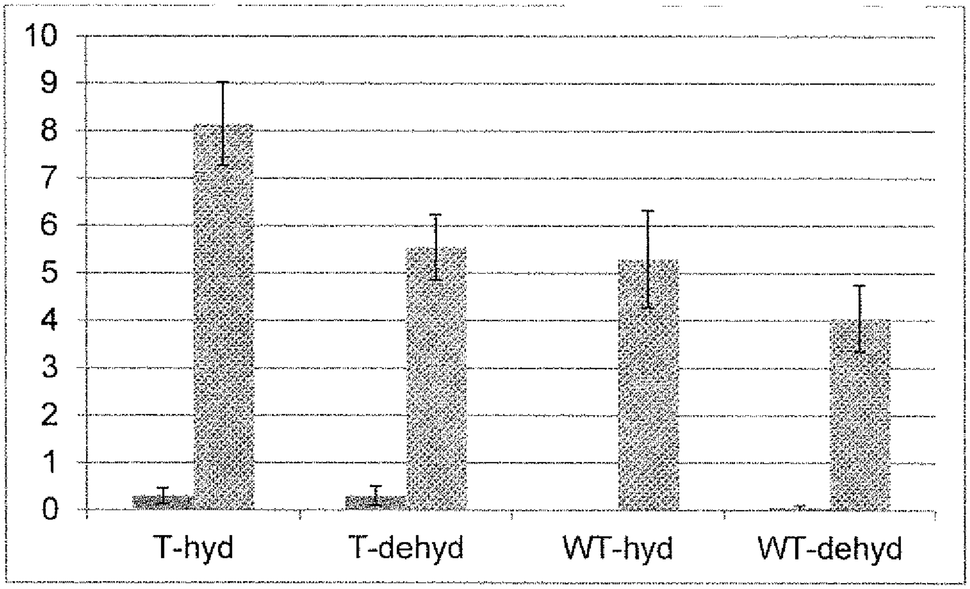
FIG. 4: The effect of dehydration on flower formation of WT and transgenic plants. The bars reflect a shift in pod formation over a 11 day period in mature plants.

The Effect of Dehydration on Seed Pods and Flowers of Wild Type Control and Transgenic Tobacco Plants Transgenic plants (fully hydrated) reached maturity significantly earlier than the wild type counterparts as evidenced by the higher number of pods (FIG. 3) and flowers (FIG. 4) observed. For those transgenic plants that were dehydrated there was also an observable difference in the number of pods and flowers compared to wild type plants (FIGS. 3 and 4).

REFERENCES

Szymczak A. L. et al (2005) Expert Opin. Biol. Ther. 5: 627-638

The invention claimed is:

1. A recombinant nucleic acid molecule comprising a nucleic acid construct operably linked to an abiotic stress inducible promoter, wherein the nucleic acid construct consists of the nucleotide sequence of SEQ ID NO: 1.

2. The recombinant nucleic acid molecule of claim 1, wherein the abiotic stress is selected from the group consisting of osmotic stress, dehydration stress, temperature stress, drought, salinity and desiccation.

3. The recombinant nucleic acid molecule of claim 1, wherein the abiotic stress inducible promoter comprises the nucleotide sequence of SEQ ID NO: 2.

4. A vector comprising the recombinant nucleic acid molecule of claim 1.

5. A host cell transformed with the vector of claim 4.

6. The host cell of claim 5, wherein the host cell is a plant cell.

7. The host cell of claim 5, wherein the host cell is stably transformed with the recombinant nucleic acid molecule.

8. A transgenic plant comprising the recombinant nucleic acid molecule of claim 1.

9. The transgenic plant of claim 8, wherein the plant is selected from the group consisting of alfalfa, barley, canola, cassava, cotton, maize, oats, rye, sorghum, soybean, sunflower, sweet potato, tobacco and wheat.

10. A transgenic seed comprising the recombinant nucleic acid molecule of claim 1.

11. A method of producing an abiotic stress tolerant transgenic plant, the method comprising stably transforming a plant with the recombinant nucleic acid molecule of claim 1 to produce said abiotic stress tolerant transgenic plant.

12. A transgenic plant comprising the host cell of claim 6.

13. The transgenic plant of claim 12, wherein the plant is selected from the group consisting of alfalfa, barley, canola, cassava, cotton, maize, oats, rye, sorghum, soybean, sunflower, sweet potato, tobacco and wheat.

* * * * *